| United States Patent [19] | [11] Patent Number: 4,631,151 |
| Kobayashi et al. | [45] Date of Patent: Dec. 23, 1986 |

[54] METHOD FOR PRODUCTION OF FLUORINE-CONTAINING AROMATIC DERIVATIVE

[75] Inventors: Michio Kobayashi; Masato Yoshida, both of Tokyo; Hideo Sawada, Aichi; Hidehiko Hagii, Aichi; Kazuyoshi Aoshima, Aichi, all of Japan

[73] Assignee: Nippon Oil & Fars Co., Ltd., Tokyo, Japan

[21] Appl. No.: 702,632

[22] Filed: Feb. 19, 1985

[30] Foreign Application Priority Data

Feb. 27, 1984 [JP]  Japan .................................. 59-34400

[51] Int. Cl.⁴ ......................... C09F 7/00; C07C 19/08
[52] U.S. Cl. .................................... 260/408; 560/130; 560/139; 562/605; 568/655; 568/936; 570/142; 570/144; 570/145; 558/425
[58] Field of Search ....................... 570/144, 142, 145; 568/936, 655, 634, 560, 566; 562/605, 145; 260/408, 465 G; 585/454; 560/139, 130

[56] References Cited

U.S. PATENT DOCUMENTS

| 3,326,928 | 6/1967 | Mattson | 570/144 |
| 3,461,155 | 8/1969 | Rice | 562/605 |
| 4,030,994 | 6/1977 | Kollonitsch | 562/605 |

OTHER PUBLICATIONS

Zhao et al., J. Org. Chem., vol. 48, pp. 4908–4910 (1983).

*Primary Examiner*—James H. Reamer
*Attorney, Agent, or Firm*—Oblon, Fisher, Spivak, McClelland & Maier

[57] ABSTRACT

A fluorine-containing aromatic derivative is produced by causing a di(haloacyl)peroxide to react upon benzene, a mono-substituted benzene, naphthalene, or a mono-substituted naphthalene thereby introducing an $X(CF_2)_n$-group into the benzene ring or the naphthalene ring.

14 Claims, No Drawings

METHOD FOR PRODUCTION OF FLUORINE-CONTAINING AROMATIC DERIVATIVE

BACKGROUND OF THE INVENTION

This invention relates to a method for the production of a fluorine-containing aromatic derivative, and more particularly to a fluorine-containing aromatic derivative useful for industrial applications.

In recent years, the reaction which, by the introduction of a perfluoroalkyl group into the molecule of an organic compound, produces a partially fluoro compound exhibiting useful properties relative to physiological activities is attracting attention.

This invention, as described above, is directed to a method for the production of a fluorine-containing aromatic derivative. For the perfluoroalkylation of aromatic compounds, various methods have been disclosed.

For example, the synthesis of a fluorine-containing aromatic derivative by the reaction of a fluorine-containing aliphatic iodide with a halogen-substituted aromatic compound under the action of ultrasonic waves in the presence of zinc powder and a palladium type catalyst (Japanese Patent Disclosure SHO No. 58(1983)-92627) and the method resorting to what is known as Ullman reaction, such as, for example, the production of 2-trifluoromethyl naphthalene by the reaction of 2-iodonaphthalene with trifluoromethyl iodide in pyridine as a solvent in the presence of copper powder as a catalyst at 120° C. (Journal of Japan Chemical Society, No. 11, 1976, page 1791) have been reported.

These methods are not advantageous commercially because they have drawbacks, specifically the former method suffering from high cost of the palladium catalyst and inevitably requiring use of ultrasonic waves and the latter method entailing difficulty in the preparation of copper powder of high catalytic activity and suffering the yield of product to be governed by the amount of the catalyst used.

The synthesis of a fluorine-containing aromatic derivative by the direct thermal reaction of a fluorine-containing aliphatic iodide with an aromatic compound instead of the aforementioned cross-coupling reaction using a metal complex has been reported (Journal of Fluorine Chemistry, Vol. 17, page 345 (1981)).

This method, however, does not provide commercially advantageous production of the derivative because the yield of the product is low (about 50%) and further because the reaction proceeds only at a high temperature (about 200° C.) and requires much time (about 50 hours) for its completion.

With a view to alleviating reaction conditions, the method of introducing a perfluoroalkyl group into aromatic compound by directly fluorinating ($R_f$-$IF_2$) a fluorine-containing aliphatic iodide ($R_f$-I) with fluorine gas, then treating the resultant fluorination product with sulfonic acid ($CF_3SO_3H$) and benzene (PhH) or fluorobenzene thereby forming a salt (1), and causing this salt (1) to react with an aromatic compound (ArH) as shown by the following formula (1) has been reported (Journal of Organic Synthetic Chemical Society, Vol. 41, No. 3, page 251 (1983)).

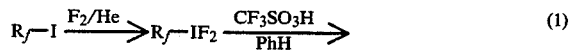

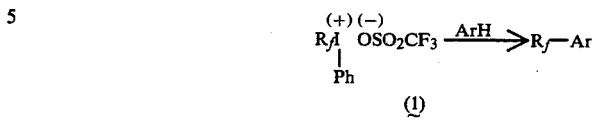

This method again proves commercially disadvantageous in respect that the aforementioned salt (1) is thermally instable, the synthesis is difficult to carry out, and the synthesis requires use of a special device.

Besides the methods described above, the reaction which uses heptafluorobutyryl peroxide as a perfluoroacyl peroxide and p-methoxy toluene and p-dimethoxybenzene derivative as aromatic compounds has been reported (the Journal of Organic Chemistry, Vol. 48, page 4908 (1983)).

In an aromatic compound having two or more substituents as described above, particularly a poly-substituted aromatic compound having attached thereto such an electron-donating group as methoxy group, the product of the introduction of a heptafluoropropyl group (n—$C_3F_7$—) is obtained in a low yield owing to the reaction of electron transfer with the heptafluorobutyryl peroxide and conversely the product of the introduction of an ester group

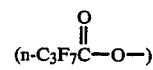

is obtained in a high yield. Particularly when the aromatic compound is p-dimethoxybenzene, 1,4-dimethyl-2,5-dimethoxybenzene, or 1,4-di-t-butyl-2,5-dimethoxybenzene, absolutely no product incorporating a heptafluoropropyl group is obtained and, instead, a product incorporating an ester group is obtained in a yield exceeding 90%.

Thus, no method has been available for commercially advantageous production of a fluorine-containing aromatic derivative by the introduction of a perfluoroalkyl group into an aromatic compound. The desirability of developing a method capable of commerically advantageously producing a fluorine-containing aromatic derivative has found widespread acceptance.

SUMMARY OF THE INVENTION

The inventors, therefore, continued a diligent study in search of a method capable of producing a desired fluorine-containing aromatic derivative in a high yield by the introduction of a perfluoroalkyl group into an aromatic compound. They have consequently found that the reaction of a specific aliphatic di(haloacyl)-peroxide with benzene or mono-substituted benzene or naphthalene or a mono-substituted naphthalene readily produces quickly and in a high yield a fluorine-containing aromatic derivative incorporating therein a fluorine-containing aliphatic group instead of a fluorine-containing aliphatic ester group. This knowledge has led to the present invention.

To be specific, the present invention relates to a method for the production of a fluorine-containing aromatic derivative by causing a di(haloacyl)peroxide of the general formula (2):

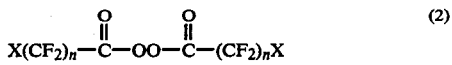

wherein X denotes a fluorine, chlorine, or hydrogen atom and n denotes an integer of the value of 1 to 10) to react with benzene or a mono-substituted benzene or naphthalene or a mono-substituted naphthalene thereby introducing the $X(CF_2)_n$-group of the aforementioned peroxide into the benzene ring or naphthalene ring.

DESCRIPTION OF THE PREFERRED EMBODIMENTS

It is believed that since benzene or a mono-substituted benzene or naphthalene or a mono-substituted naphthalene is used as the aromatic compound in the reaction of the present invention, the di(haloacyl)peroxide, during thermal decomposition, undergoes a concerted radical decomposition as shown by the following formulas (3), (4), and (5) and gives rise to a fluoroalkyl radical and then reacts with the aromatic compound and, therefore, enables the aromatic compound to be fluoroalkylated efficiently in a high yield.

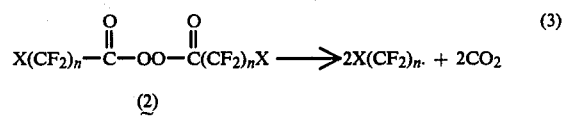

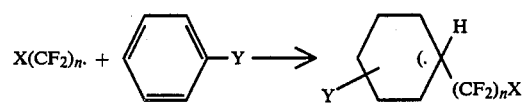

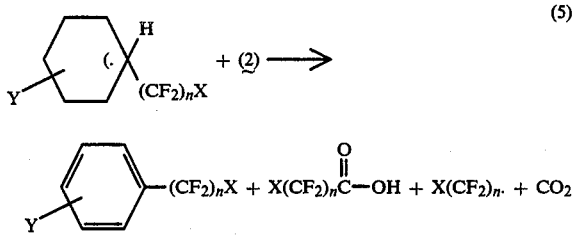

(wherein X denotes a fluorine, chloride, or hydrogen atom, Y denotes a hydrogen atom, a halogen atom, an alkyl group, a nitro group, an ester group, or an alkoxy group, and n denotes an integer of the value of 1 to 10).

This invention is characterized by using a di(haloacyl)peroxide represented by the formula (2). Even when benzene is caused to react with an aliphatic diacylperoxide not substituted with fluorine such as, for example, di-iso-butyryl peroxide, cumene which is a corresponding aromatic derivative in the aforementioned reaction formula is produced only in a minute amount.

This invention uses a di(haloacyl)peroxide of the aforementioned formula having n as an integer of the value of 1 to 10 because it pays due respect to the solubility of the peroxide in the reaction solvent, particularly a halogenated aliphatic solvent. If the value of n exceeds 10, the solubility of the peroxide is not sufficient.

Concrete examples of the di(haloacyl)peroxide represented by the formula (2) to be used in this invention include bis(trifluoroacetyl)peroxide, bis(pentafluoropropionyl)peroxide, bis(heptafluorobutyryl)peroxide, bis(nonafluoropentanoyl)peroxide, bis(undecafluorohexanoyl)peroxide, bis(tridecafluoroheptanoyl)peroxide, bis(pentadecafluorooctanoyl)-peroxide, bis(heptadecafluoropelargonyl)peroxide, bis(nonadecafluorodecanoyl)peroxide, bis(heneicosafluoroundecanoyl)peroxide, bis(chlorodifluoroacetyl)peroxide, bis(3-chlorotetrafluoropropionyl)peroxide, bis(4-chlorohexafluorobutyryl)peroxide, bis(5-chlorooctafluoropentanoyl)peroxide, bis(6-chlorodecafluorohexanoyl)peroxide, bis(7-chlorododecafluoroheptanoyl)peroxide, bis(8-chlorotetradecafluorooctanoyl)peroxide, bis(9-chlorohexadecafluoropelargonyl)peroxide, bis(10-chlorooctadecafluorodecanoyl)peroxide, bis(11-chloroeicosafluoroundecanoyl)-peroxide, bis(2-H-difluoroacetyl)peroxide, bis(3-H-tetrafluoropropionyl)-peroxide, bis(4-H-hexafluorobutyryl)peroxide, bis(5-H-octafluoropentanoyl)-peroxide, bis(6-H-decafluorohexanoyl)peroxide, bis(7-H-dodecafluoroheptanoyl)peroxide, bis(8-H-tetradecafluorooctanoyl)peroxide, bis(9-H-hexadecafluoropelargonyl)peroxide, bis(10-H-octadecafluorodecanoyl)-peroxide, and bis(11-H-eicosafluoroundecanoyl)-peroxide.

Among the di(haloacyl)peroxides enumerated above, particularly advantageous from the practical point of view are bis(trifluoroacetyl)peroxide, bis(pentafluoropropionyl)peroxide, bis(heptafluorobutyryl)peroxide, bis(nonafluoropentanoyl)peroxide, bis(undecafluorohexanoyl)peroxide, bis(tridecafluoroheptanoyl)peroxide, bis(pentadecafluorooctanoyl)peroxide, bis(heptadecafluoropelargonyl)-peroxide, bis(nonadecafluorodecanoyl)peroxide, bis(heneicosafluoroundecanoyl)peroxide, bis(4-chlorohexafluorobutyryl)-peroxide, and bis(4-H-hexafluorobutyryl)peroxide.

The aromatic compound which incorporates the $X(CF_2)_n$-group by reaction with the di(haloacyl)-peroxide is any one selected from among benzene, mono-substituted benzenes, naphthalene, and mono-substituted naphthalenes.

Examples of mono-substituted benzene include chlorobenzene, fluorobenzene, bromobenzene, iodobenzene, toluene, ethylbenzene, cumene, n-propylbenzene, nitrobenzene, phenyl acetate, phenyl propionate, anisole, ethoxybenzene, and benzonitrile. The substituents of these mono-substituted benzenes are desired to be halogen atoms, alkyl groups, nitro groups, ester groups, and alkoxy groups. Particularly desirable substituents are alkyl groups, alkoxy groups, and ester groups having not more than three carbon atoms.

Examples of the mono-substituted naphthalene which proves desirable include 1-iodonaphthalene, 1-bromonaphthalene, 1-chloronaphthalene, 2-iodonaphthalene, 2-bromonaphthalene, and 2-chloronaphthalene which have halogen atoms as substituents.

The di(haloacyl)peroxide of the aforementioned formula (2) to be used in the present invention, during the course of production and handling, is desired to be in a form diluted in a solvent. The solvent is desired to be a halogenated aliphatic solvent which contains no hydrogen atom.

Concrete examples of the solvent include 2-chloro-1,2-dibromo-1,1,2-trifluoroethane, 1,2-dibromohexafluoropropane, 1,2-dibromotetrafluoroethane, 1,1-difluorotetrachloroethane, 1,2-difluorotetrachloroethane, fluorotrichloromethane, heptafluoro-2,3,3-trichlorobutane, 1,1,1,3-tetrachlorotetrafluoropropane, 1,1,1-trichloropentafluoropropane, 1,1,1-trichlorotrifluoroethane, and 1,1,2-trichlorotrifluoroethane. Among the halogenated aliphatic solvents cited above, 1,1,2-trichlorotrifluoroethane proves particularly desirable for the purpose of commercial production of the fluorine-containing aromatic derivative aimed at by this invention.

Now, the conditions under which the reaction of the di(haloacyl)peroxide represented by the formula (2) with the aforementioned aromatic compound proceeds will be described.

The molar ratio in which the di(haloacyl)-peroxide and the aromatic compound are combined in preparation for the reaction is desired to fall in the range of 1:2~10, preferably 1:4~7. If the latter number of the molar ratio relative to the former (unity) is less than 2, the fluorine-containing aromatic derivative produced by the reaction tends to suffer from a low yield. If that number exceeds 10, the solubility of the solid aromatic compound (mono-substituted benzene, naphthalene, or mono-substituted naphthalene) suffers from insufficient solubility and the unaltered aromatic compound occurs in a large amount after completion of the reaction and the isolation of the product aimed at is difficult to attain.

The reaction can be carried out under atmospheric pressure at temperatures generally in the range of 0° to 50° C., preferably 20° to 40° C. If the reaction temperature is less than 0° C., the reaction time is liable to increase. If it exceeds 50° C., the pressure increases during the course of the reaction, making the operation of the reaction difficult to control.

Now, the characteristics of the method of this invention will be enumerated below.

(1) By the aforementioned di(haloacyl)-peroxide, the X(CF$_2$)$_n$-group is quickly, efficiently, and easily incorporated in the benzene ring or naphthalene ring to permit production of the fluorine-containing aromatic derivative aimed at without requiring any reaction catalyst or any special device.

(2) Despite the use of a fluorine-containing peroxide during the course of the reaction, the fluorine-containing aromatic derivative aimed at can be produced safely.

(3) The reaction by-produces a fluorine-containing fatty acid substantially in an equal mol to the fluorine-containing derivative. This fatty acid is expensive and finds utility in various applications. It may be chlorinated into an acid chloride, which is further converted into di(haloacyl)peroxide and thus advantageously used again in the present invention.

(4) The fluorine-containing aromatic derivative to be produced by the method of this invention is useful as an intermediate for the synthesis of medicines, agricultural pesticides, and water-repellent oil-repellent agents.

Now, the present invention will be described more specifically below with reference to working examples and comparative experiments.

The kinds, amounts, and molar ratios of di(haloacyl)-peroxides and aromatic compounds used, the reaction conditions involved, and the kinds and yields of fluorine-containing aromatic derivatives and by-products obtained in Examples 1-16 are shown in the following tables.

The working examples will be cited below.

EXAMPLE 1

A solution of 16.52 g (0.02 mol) of bis(pentadecafluorooctanoyl)peroxide in 100 ml of 1,1,2-trichlorotrifluoroethane was placed in a flask and then 7.81 g (0.10 mol) of benzene was added. After this addition, the reactants were maintained at 40° C. as swept with a current of nitrogen gas and thus left reacting for three hours. Analysis of the reaction product by gas chromatography revealed that the reaction produced pentadecafluoroheptylbenzene in a yield of 98%. The reaction also by-produced pentadecafluorocaprylic acid in a yield of 99%.

The reaction product was washed with 200 ml of an aqueous sodium hydroxide solution and distilled to exclude 1,1,2-trichlorotrifluoroethane. In the distillation, pentadecafluoroheptylbenzene was isolated at b.p. 198° to 198° C.

The aforementioned yields were based on bis(pentadecafluorooctanoyl)peroxide.

EXAMPLE 2

The procedure of Example 1 was repeated, except that bis(heptafluorobutyryl)peroxide was used in the place of bis(pentadecafluorooctanoyl)peroxide.

EXAMPLES 3-5

The procedure of Example 1 was repeated under varying conditions shown in the table, except that benzene was changed respectively to toluene, chlorobenzene, and bromobenzene.

EXAMPLES 6-7

The procedure of Example 1 was repeated under conditions shown in the table, except that bis(pentadecafluorooctanoyl)peroxide was changed to bis(heptafluorobutyryl)peroxide, benzene was changed respectively to naphthalene and toluene, and use of the solvent was omitted in Example 7.

EXAMPLES 8-11

The procedure of Example 1 was repeated under varying conditions shown in the table, except that bis(pentadecafluorooctanoyl)peroxide was changed respectively to bis(4-chlorohexafluorobutyryl)-peroxide, bis(trifluoroacetyl)peroxide, bis(4-H-hexafluorobutyryl)-peroxide and bis(heneicosafluoroundecanoyl)peroxide.

EXAMPLES 12-13

The procedure of Example 1 was repeated under the conditions shown in the table, except that the amounts of benzene and the reaction temperatures were changed.

EXAMPLES 14-15

The procedure of Example 1 was repeated under the conditions shown in the table, except that bis(pentadecafluorooctanoyl)peroxide was changed to bis(heptafluorobutyryl)peroxide and benzene was changed to anisole and phenyl acetate.

EXAMPLE 16

The procedure of Example 1 was repeated under the conditions shown in the table, except that bis(pentadecafluorooctanoyl)peroxide was changed to bis(heptafluorobutyryl)peroxide and benzene was changed to 1-chloronaphthalene.

| Example No. | | | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| Di(haloacyl)peroxide | X | | F | F | F | F | F | F | F | Cl | F | H | F | F | F | F | F | F |
| $(X(CF_2)_n-\overset{O}{\underset{\|}{C}}-O)_2$ | n | | 7 | 3 | 7 | 7 | 7 | 3 | 3 | 3 | 1 | 3 | 10 | 7 | 7 | 3 | 3 | 3 |
| | Amount | (g) | 16.52 | 8.52 | 16.52 | 16.52 | 16.52 | 8.52 | 8.52 | 9.18 | 4.52 | 9.18 | 11.26 | 16.52 | 16.52 | 8.52 | 8.52 | 8.52 |
| | | (mol) | 0.02 | 0.02 | 0.02 | 0.02 | 0.02 | 0.02 | 0.02 | 0.02 | 0.02 | 0.02 | 0.01 | 0.02 | 0.02 | 0.02 | 0.02 | 0.02 |
| Aromatic compound | Benzene | | | | | | | | | | | | | | | | | |
| |  Y | | | | | | | | | | | | | | | | | |
| | Amount | (g) | 7.81 | 7.81 | | | | | | | | 7.81 | 7.81 | 4.69 | 7.81 | | | |
| | | (mol) | 0.10 | 0.10 | | | | | | | | 0.10 | 0.10 | 0.06 | 0.10 | | | |
| | Y | | | | $CH_3$ | Cl | Br | | $CH_3$ | H | | | | | | | | |
| | Mono-substituted benzene | Amount (g) | | | 9.21 | 11.26 | 15.70 | | 9.21 | 7.81 | | | | | | | 13.62 | |
| | | Amount (mol) | | | 0.10 | 0.10 | 0.10 | | 0.10 | 0.10 | | | | | | | 0.10 | |
| | Naphthalene | Amount (g) | | | | | | 12.82 | | | 9.37 | | | | | 14.06 | | |
| | | Amount (mol) | | | | | | 0.10 | | | 0.12 | | | | | 0.13 | | |
| |  Z | | | | | | | | | | | | | | | | $OCH_3$ | $O-\overset{O}{\underset{\|}{C}}-CH_3$ | Cl |
| | Mono-substituted naphthalene | Amount (g) | | | | | | | | | | | | | | | | | 16.26 |
| | | Amount (mol) | | | | | | | | | | | | | | | | | 0.10 |
| Molar ratio of di(haloacyl)peroxide to aromatic compound | | | 1:5 | 1:5 | 1:5 | 1:5 | 1:5 | 1:5 | 1:5 | 1:5 | 1:6 | 1:5 | 1:10 | 1:3 | 1:5 | 1:6.5 | 1:5 | 1:5 |
| Reaction conditions | Temperature (°C.) | | 40 | 40 | 40 | 40 | 40 | 35 | 0 | 40 | 30 | 35 | 15 | 40 | 20 | 20 | 35 | 40 |
| | Time (hr) | | 3 | 3 | 2 | 5 | 6 | 4 | 5 | 3 | 5 | 4 | 5 | 3 | 9 | 6 | 6 | 7 |

| Example No. | 1 | 2 | 3 | 4 | 5 | 6 | 7 | 8 |
|---|---|---|---|---|---|---|---|---|
| Fluorine-containing derivative aimed at |  | | | | | | | |
| Yield | 98 | 94 | 92 | 90 | 91 | 89 | 86 | 92 |
| By-product of reaction | n-$C_7F_{15}\overset{O}{\underset{\|}{C}}$—OH | n-$C_3F_7\overset{O}{\underset{\|}{C}}$—OH | n-$C_7F_{15}\overset{O}{\underset{\|}{C}}$—OH | n-$C_7F_{15}\overset{O}{\underset{\|}{C}}$—OH | n-$C_7F_{15}\overset{O}{\underset{\|}{C}}$—OH | n-$C_7F_{15}\overset{O}{\underset{\|}{C}}$—OH | n-$C_3F_7\overset{O}{\underset{\|}{C}}$—OH | Cl($CF_2$)$_3\overset{O}{\underset{\|}{C}}$—OH |
| Yield | 99 | 97 | 90 | 93 | 95 | 90 | 90 | 89 |

| Example No. | 9 | 10 | 11 | 12 | 13 | 14 | 15 | 16 |
|---|---|---|---|---|---|---|---|---|
| Fluorine-containing derivative aimed at | | | | | | | | |
| Yield | 93 | 96 | 89 | 85 | 87 | 82 | 86 | 86 |
| By-product of reaction | $CF_3\overset{O}{\underset{\|}{C}}$—OH | H($CF_2$)$_3\overset{O}{\underset{\|}{C}}$—OH | n-$C_{10}F_{21}\overset{O}{\underset{\|}{C}}$—OH | n-$C_7F_{15}\overset{O}{\underset{\|}{C}}$—OH | n-$C_7F_{15}\overset{O}{\underset{\|}{C}}$—OH | n-$C_3F_7\overset{O}{\underset{\|}{C}}$—OH | n-$C_3F_7\overset{O}{\underset{\|}{C}}$—OH | n-$C_3F_7\overset{O}{\underset{\|}{C}}$—OH |
| Yield | 96 | 85 | 93 | 87 | 91 | 85 | 87 | 88 |

COMPARATIVE EXPERIMENT 1

The procedure of Example 1 was repeated, except that bis(pentadecafluorooctanoyl)peroxide was changed to bis(heptafluorobutyryl)peroxide and benzene was changed to 1,4-di-t-butyl-2,5-dimethoxybenzene, with the reaction temperature fixed at 5° C. and the reaction time at 15 hours. The product obtained by the reaction was mixture of compounds having the ester group

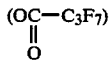

introduced at different positions (93% and 5% in yield). No product incorporating a fluorine-containing aliphatic group (—$C_3F_7$, in the present case) was obtained.

The results indicate that the introduction of a fluorine-containing aliphatic group is not obtained by the use of a di-substituent of aromatic compound.

COMPARATIVE EXPERIMENT 2

The procedure of Example 1 was repeated, except that bis(pentadecafluorooctanoyl)peroxide was changed to di-iso-butyryl peroxide, the amount of benzene was changed to 0.02 mol, the reaction temperature was changed to 46° C., and the reaction time was fixed at 9 hours. Consequently, cumene was obtained in a yield of 0.8%.

The results indicate that when an aliphatic diacylperoxide not substituted with fluorine and an aromatic compound are subjected to the reaction contemplated by the present invention, an aromatic derivative incorporating an aliphatic group is obtained only in a minute amount.

It is evident from the examples and the comparative experiments cited above that the aromatic compounds to which the incorporation of an $X(CF_2)_n$-group is accomplished by the use of a di(haloacyl)peroxide represented by the formula (2) as contemplated by the present invention are benzene, mono-substituted benzenes, naphthalene, and mono-substituted naphthalenes. In the working examples, the fluorine-containing aromatic derivatives aimed at were invariably obtained in high yields.

The data clearly show that the present invention is highly practicable as compared with the conventional method.

What is claimed is:

1. A method for the production of a fluorine-containing derivative of an aromatic compound by introducing an $X(CF_2)_n$—group, wherein X is fluorine, chlorine or hydrogen and n is an integer having a vlaue of 1 to 10, into an aromatic ring of the aromatic compound, which comprises the steps of:

reacting a de(haloacyl)peroxide represented by the general formula:

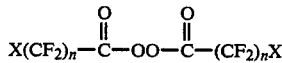

wherein X and n are as defined above with an aromatic compound selected from the group consisting of (a) benzene, (b) a mono-substituted benzene in which the substituent is a member selected from the group consisting of halogen, alkyl, nitro, ester and alkoxy groups, (c) naphthalene and (d) a monohalo-substituted naphthalene at a temperature 0° to 50° C. at a molar ratio of said di(haloacyl)peroixde to said aromatic compound in the range of 1:2 to 10; and refining the reaction products to obtain a fluorine-containing derivative of the aromatic compound having the $X(CF_2)_n$—group introduced into the aromatic ring thereof.

2. The method according to claim 1, wherein said aromatic compound is benzene.

3. The method according to claim 1, wherein said aromatic compound is naphthalene.

4. The method according to claim 1, wherein the substituent of said mono-substituted benzene compound is selected from the group consisting of alkyl, alkoxy and ester groups having not less than 3 carbon atoms.

5. The method according to claim 1, wherein said aromatic compound is said monohalo-substituted naphthalene compound.

6. The method according to claim 1, wherein said di(haloacyl)peroxide is diluted with a halogenated aliphatic solvent which contains no hydrogen atoms before the reaction with said aromatic compound.

7. The method according to claim 1, wherein said mono-substituted benzene compound is chlorobenzene, fluorobenzene, bromobenzene, iodobenzene, toluene, ethylbenzene, cumene, n-propylbenzene, nitrobenzene, phenyl acetate, phenyl propionate, anisole, ethoxybenzene or benzonitrile.

8. The method according to claim 1, wherein said monohalo-substituted naphthlene compound is 1-iodonaphthalene, 1-bromonaphthalene, 1-chloro-naphthalene, 2-iodonaphthalene, 2-bromonaphthalene, or 2-chloronaphthalene.

9. The method according to claim 1, wherein said di(haloacyl)peroxide is bis(trifluoroacetyl)peroxide, bis(pentafluoropropionyl)peroxide, bis(heptafluorobutyryl)peroxide, bis(nonafluoropentanoyl)peroxide, bis(undecafluorohexanoyl)peroxide, bis(tridecafluoroheptanoyl)peroxide, bis(pentadecafluorooctanoyl)peroxide, bis(heptadecafluoropelargonyl)peroxide, bis(nonadecafluorodecanoyl)-peroxide, bis(heneicosafluorodecanoyl)peroxide, bis(chlorodifluoroacetyl)peroxide, bis(3-chlorotetrafluoropropionyl)peroxide, bis(4-chlorohexafluorobutyryl)peroxide, bis(5-chlorooctafluoropentanoyl)-peroxide, bis(6-chlorodecafluorohexanoyl)peroxide, bis(7-chlorododecafluoroheptanoyl)peroxide, bis(8-chlorotetradecafluorooctanoyl)peroxide, bis(9-chlorohexadecafluoropelargonyl)peroxide, bis(10-chlorooctadecafluorodecanoyl)peroxide, bis(11-chloroeicosafluoroundecanoyl)peroxide, bis(2-H-difluoroacetyl)peroxide, bis(3-H-tetrafluoropropionyl)peroxide, bis(4-H-hexafluorobutyryl)peroxide, bis(5-H-octafluoropentanoyl)-peroxide, bis(6-H-decafluorohexanoyl)peroxide, bis(7-H-dodecafluoroheptanoyl)peroxide, bis(8-H-tetradecafluorooctanoyl)peroxide, bis(9-H-hexadecafluoropelargonyl)-peroxide, bis(10-H-octadecafluorodecanoyl)-peroxide, or bis(11-H-eicosafluoroundecanoyl)peroxide.

10. The method according to claim 9, wherein said di(haloacyl)peroxide is bis(trifluoroacetyl)-peroxide, bis(pentafluoropropionyl)peroxide, bis(heptafluorobutyryl)peroxide, bis(nonafluoropentanoyl)peroxide, bis(undecafluorohexanoyl)peroxide, bis(tridecafluoroheptanoyl)peroxide, bis(pentadecafluorooctanoyl)peroxide, bis(heptadecalfluoropelargonyl)peroxide, bis(nonadecafluorodecanoyl)-peroxide, bis(heneicosafluoroundecanoyl)peroxide, bis(4-chlorohexafluorobutyryl)peroxide, or bis(4-H-hexafluorobutyryl)peroxide.

11. The method according to claim 6, wherein said halogenated solvent is 2-chloro-1,2-dibromo-1,1,2-trifluoroethane, 1,2-dibromohexafluoropropane, 1,2-dibromotetrafluoroethane, 1,1-difluorotetrachloroethane, 1,2-difluorotetrachloroethane, fluorotrichloromethane, heptafluoro-2,3,3-trichlorobutane, 1,1,1,3-tetrachlorotetrafluoropropane, 1,1,1-trichloropentafluoropropane, 1,1,1-trichlorotrifluoroethane, or 1,1,2-trichlorotrifluoroethane.

12. The method according to claim 11, wherein said solvent is 1,1,2-trichlorotrifluoroethane.

13. The method according to claim 1 wherein the molar ratio of said di(haloacyl)peroxide aromatic compound ranges from 1:4–7.

14. The method according to claim 1, wherein the temperature of said reaction ranges from 20° to 40° C.

* * * * *